(12) United States Patent
Strecker

(10) Patent No.: US 6,485,524 B2
(45) Date of Patent: *Nov. 26, 2002

(54) STENT FOR TREATING PATHOLOGICAL BODY VESSELS

(76) Inventor: Ernst-Peter Strecker, Vierordt Str 7A, 76228 Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,714

(22) Filed: Feb. 16, 1999

(65) Prior Publication Data

US 2001/0003801 A1 Jun. 14, 2001

Related U.S. Application Data

(63) Continuation of application No. PCT/DE98/00226, filed on Jan. 24, 1998.

(30) Foreign Application Priority Data

Jan. 31, 1997 (DE) .......................................... 197 03 482

(51) Int. Cl.⁷ .................................................. A61F 2/06
(52) U.S. Cl. ...................................... 623/122; 623/1.15
(58) Field of Search ............................. 623/1, 12, 1.15, 623/1.22, 1.51, 1.53, 1.54, 1.16; 606/194, 200

(56) References Cited

U.S. PATENT DOCUMENTS

| 5,015,253 A | * | 5/1991 | MacGregor ..................... 623/1 |
| 5,061,275 A | * | 10/1991 | Wallsten et al. ............. 623/1.22 |
| 5,116,365 A | | 5/1992 | Hillstead ........................ 623/1 |
| 5,354,308 A | | 10/1994 | Simon et al. ................ 606/198 |
| 5,360,401 A | | 11/1994 | Turnland et al. ............... 604/96 |
| 5,395,390 A | | 3/1995 | Simon et al. ................ 606/198 |
| 5,405,377 A | * | 4/1995 | Cragg ............................ 623/1 |

(List continued on next page.)

FOREIGN PATENT DOCUMENTS

| DE | 44 07 079 A1 | 3/1994 |
| DE | 44 32 938 A1 | 9/1994 |
| EP | 0 556 850 A1 | 8/1993 |
| EP | 0 647 148 B1 | 6/1994 |
| WO | WO 92/05829 | 4/1992 |
| WO | WO 94/00179 | 1/1994 |
| WO | WO 95/18585 | 7/1995 |
| WO | WO 97/36556 | 10/1997 |

Primary Examiner—Corrine McDermott
Assistant Examiner—Brian E. Pellegrino
(74) Attorney, Agent, or Firm—RatnerPrestia

(57) ABSTRACT

A known method for treating pathological body vessels is the implantation of stents as an extended filament, by means of a catheter, which springs into a given form at the implantation site, as a result of its thermo-memory property or its elasticity. The invention relates to a new kind of stent, created in order to improve the flexibility and stability of the stent. This is achieved in that the stent filament or stent filaments are present in the form of at least two opposed spirals. The filament consists of a material with high elasticity or with thermo-memory properties. The stent can be covered with a structure made of pieces of fabric and/or fibers and serves in this way as a stent graft. The new stent demonstrates high stability and flexibility. The stent can be introduced into a body vessel by means of a catheter lumen, which essentially corresponds to the outside diameter of the filaments forming the stent which expands in the point of destination to a larger-lumen tube-shaped implant.

6 Claims, 13 Drawing Sheets

U.S. PATENT DOCUMENTS

| | | | |
|---|---|---|---|
| 5,464,419 A | * 11/1995 | Glastra | 606/194 |
| 5,503,636 A | * 4/1996 | Schmitt et al. | 606/194 |
| 5,540,712 A | 7/1996 | Kleshinkski et al. | 606/198 |
| 5,571,135 A | 11/1996 | Fraser et al. | 606/198 |
| 5,609,627 A | * 3/1997 | Goicoechea et al. | 623/1 |
| 5,741,332 A | * 4/1998 | Schmitt | 623/12 |
| 5,746,765 A | 5/1998 | Kleshinkski et al. | 606/198 |
| 5,830,229 A | 11/1998 | Konya et al. | 606/198 |
| 5,843,161 A | * 12/1998 | Solovay | 623/1 |
| 5,897,589 A | * 4/1999 | Cottenceau et al. | 623/1 |

* cited by examiner

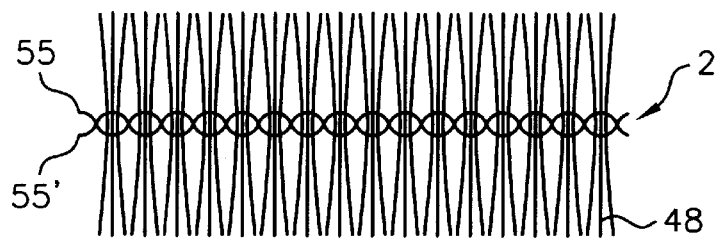
FIG. 16
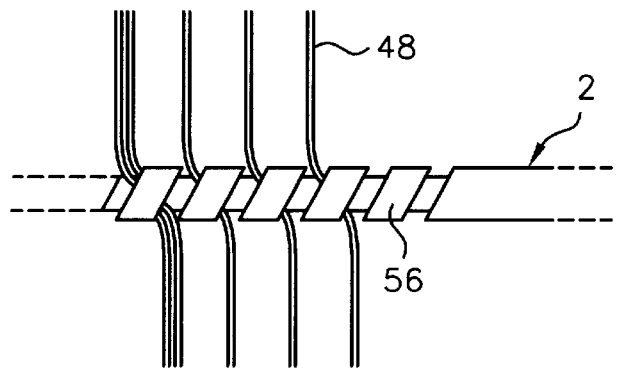
FIG. 17
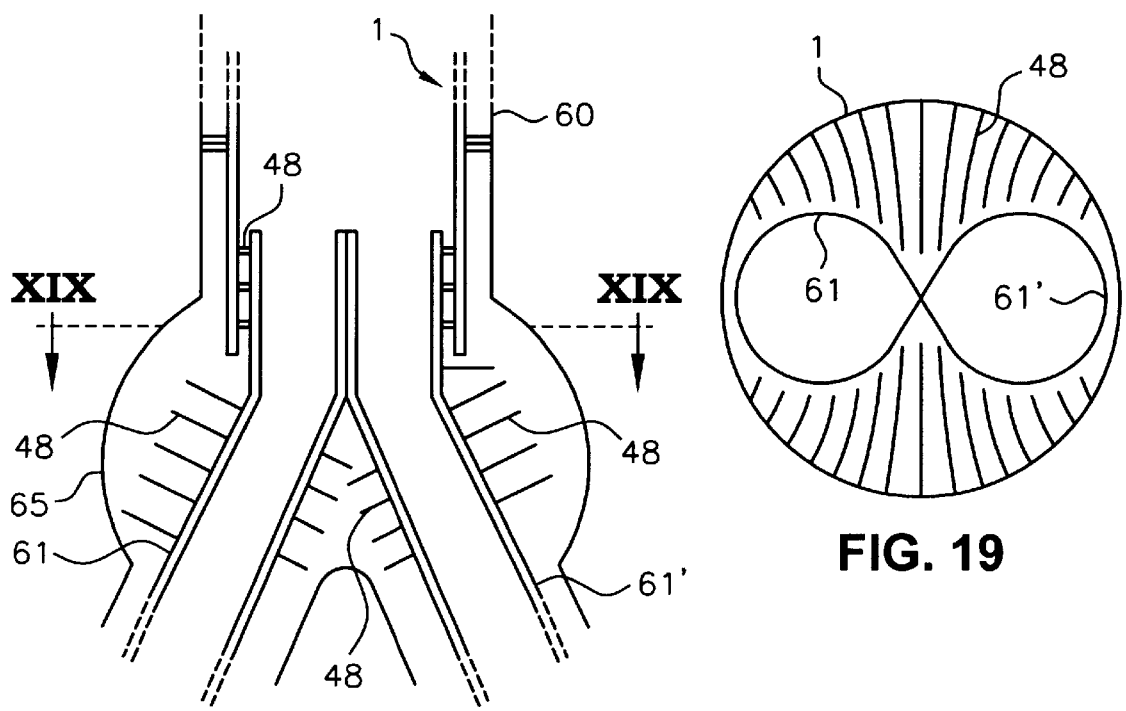
FIG. 18
FIG. 19

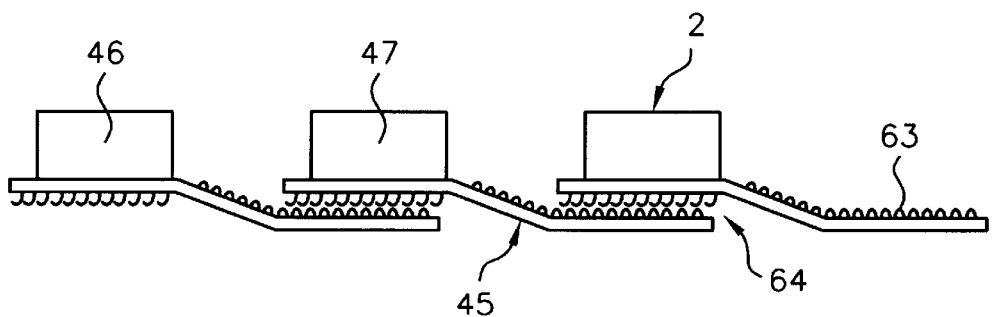
FIG. 20
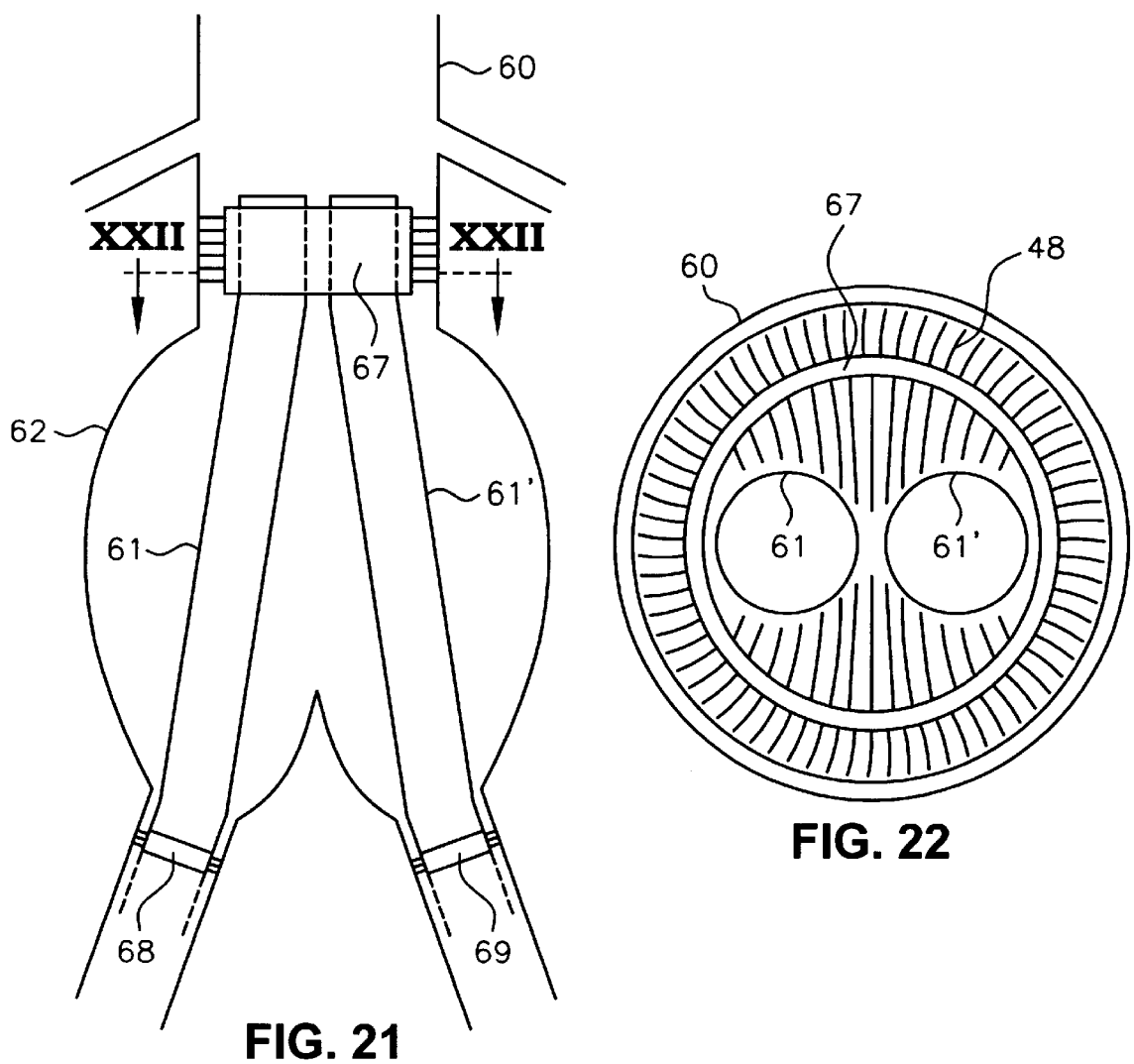
FIG. 21
FIG. 22

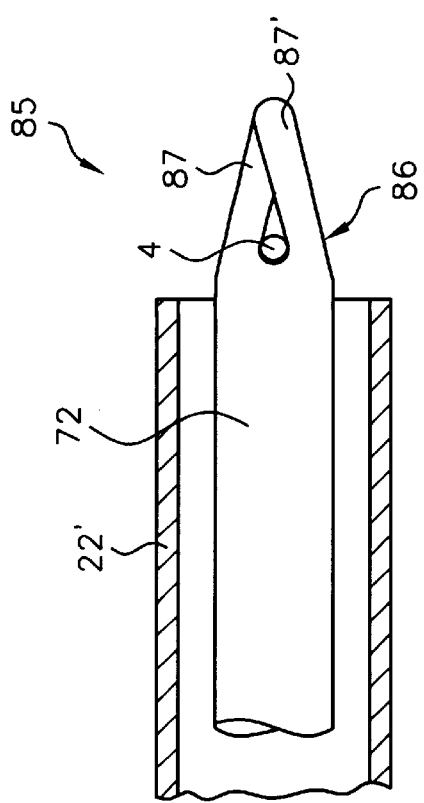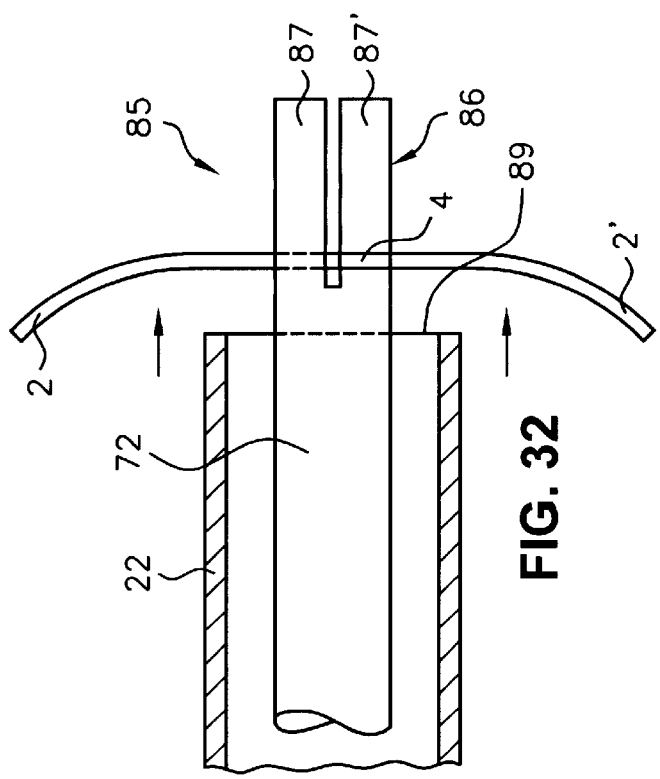

STENT FOR TREATING PATHOLOGICAL BODY VESSELS

RELATED APPLICATIONS

This application claims priority to and is a continuation of PCT/DE98/00226, filed Jan. 24, 1998, which designates the United States, and German Application No. 197 03 482.9 filed Jan. 31, 1997, the entire teachings of the above applications being incorporated herein by reference.

BACKGROUND OF THE INVENTION

The invention concerns a stent for the treatment of pathological body vessels, which can be introduced into the body vessel in the form of at least two longitudinally extended filaments by means of an implantation device and assumes its predetermined form only at the site of implantation after the implantation has been carried out.

The introduction of spiral stents of metal or plastic into a diseased body vessel for treating pathological body and blood vessels is known. Such treatments are considered for diseased vessel occlusions or aneurysms, particularly of the aorta. The implantation of such vessel prostheses is made difficult due to the considerable diameter of these prosthesis. For the most part, only one surgical implantation of the vessel prostheses is possible in combination with an opening of the vessel and a subsequent vessel closure by means of a vessel suture. In the case of treatment of an aortic aneurysm, stents are introduced by means of the pelvic arteries. This treatment is made difficult or is completely obstructed by stenoses occurring principally in combination with aortic aneurysms and by the serpentine course of the pelvic arteries.

In the named cases, but also in the case of treatment of small vessels, such as intracranial vessels, it is advantageous to use stents, which can be widened from a small diameter present during the implantation to a larger diameter at the implantation site. It is provided accordingly to implant balloon-expandable and self-widening stents with a suitable catheter in the vessels to be treated. However, up to the present time, the named stents have still not fulfilled the technical prerequisites for a problem-free insertion.

Thus, for example, in the case of the so-called IN stent, this involves an elastic spiral, which is kept at a smaller diameter during introduction in the body vessel by the catheter, is released from the catheter at the site of implantation by means of a special mechanism, and then widens to its diameter of use.

Here, there is the disadvantage that the diameter of the spiral stent is at most double in the widened state when compared with the initial state, whereby relatively large puncture openings are necessary for introducing this type of stent. In this connection, the use of a thermo-memory wire has already been described in the paper "Transluminally placed coil spring endarterial tube grafts", Invest. Radiol. (1969) No. 4, pages 329 ff. by Charles Dotter.

Thermo-memory wires are for the most part Nitinol wires, i.e., thus nickel-titanium alloys, which are brought to a predetermined form at temperatures between 400° and 500° Celsius, and keep this form up to a determined transformation temperature below body temperature.

The "thermo-memory property" is understood to mean that these wires lose their previous form and elasticity by an appropriate subsequent cooling, for example by means of ice water, and then are freely movable as longitudinally extended wire and are flexible. As soon as the wire has again warmed up to a temperature approximately corresponding to body temperature, such a wire springs back in a fully elastic manner into the spatial form impressed during the heat treatment.

Charles Dotter has proposed to implant a spiral stent from cooled thermo-memory wire in the form of a longitudinally extended wire, which then springs into the desired spiral and prosthetic form at the site of implantation, due to its described thermo-memory property. It has been shown that such simple coiled stents in their predetermined state have law stability and are also difficult to introduce and to place exactly.

A stent is known from WO 94/03127, in which several wire filaments that are longitudinally extended in an introductory shape assume in their predetermined state an undulating form that conforms to the vessel wall, whereby the wavy lines of two filaments are shaped each time such that a network comprised of approximately oval elements is formed. The stability of this network can be increased further in that wavy lines lying opposite one another are joined together at sites where they approach one another.

It is a disadvantage in this network-type stent that the implantation of such a complicated structure leads in particular to considerable difficulties in the case of greatly curved vessels. In addition, the construction of such a stent made of a multiple number of individual filaments requires a catheter with a relatively wide introduction diameter. Further, in this above-described stent, each time there is only one single predetermined diameter in the expanded or widened state. It is thus difficult to adapt the stent diameter to the diameter of the artery to be treated.

SUMMARY

The object of the present invention is thus to create a stent of the above-named type and functional purpose, which is characterized by a high stability as well as a simple handling during implantation and, in addition, has a high rate of expansion, i.e., a particularly high ratio of stent diameter in the expanded state to stent diameter in the introduction state.

This object is resolved in a stent having at least two filaments in the form of opposing spirals over at least one part of the longitudinal extent of the stent. The stent according to the invention thus exists in its predetermined state of at least two spirals, which are arranged opposite one another, thus in opposite rotational direction, and has the outer form of a tube. It is this double-spiral stent with filaments in the extended state, thus with a nearly one-dimensional structure, which is introduced.

A stent formed in this way has a high stability with a simultaneous high flexibility. The pitch of the individual spiral loops can thus be greatly modified over the entire length of the stent. This makes possible, in particular, a placement of the stent in greatly curved body vessels, without having to contend with adversely affecting the stability of the stent or damaging the lumen of the body vessel, if it becomes constricted, even if only in segments. The entire length of the stent body can also be modified due to the variability of the pitches of the individual spirals. In this way, for example, an improved anchoring of the stent within the body vessel can be achieved. Further, a varying load capacity or support capacity of the stent each time adapted to the vessel can be achieved in the treatment of vessel disorders, such as, for example, aneurysms. Spiral loops with smaller pitch, thus of higher density, are required roughly at the ends of an aneurysm stent in order to anchor the stent here, while in the region of the aneurysm itself, fewer spiral loops are required.

A particularly careful and simple implantation of the stent is then possible, if the filament is produced from a thermo-memory wire. In this connection, in particular, the use of Nitinol® wires is recommended. However, plastic filaments with suitable thermo-memory properties can also be used. Instead of the filaments produced from thermo-memory wire, high-elastic to super-elastic wires may also be selected as filaments, which arrive at the site of implantation in their predetermined spiral form, due to their special elastic properties. Such a filament can also be produced from Nitinol, from special steel, or also from suitable plastics.

Appropriately, there are two filaments, each time forming a coil of a single filament wire, which has a sharp bend, an arc-shaped piece or a loop roughly at the distal end of the stent, such that the configuration of two opposed spirals is made possible. Such a design has a high stability.

Instead of producing the double-spiral structure of the stent according to the invention from one filament wire, which is bent correspondingly into the shape of opposed spirals, it is also possible to cut the double-spiral structure of the stent from a tube-shaped workpiece. The cutting out can be produced very efficiently by means of a laser. The particular advantage of this configuration lies in the fact that the opposed spirals are already joined with one another at their crossover points, whereby possible additional connection means are not necessary.

A further stabilizing action of the stent is achieved by joining together two spirals constructed of individual filaments roughly at the distal end of the stent. This joining can be produced by gluing, soldering or welding the two stent wires, or also, however, this may involve a sleeve, which engages over the two stent wires and thus produces a connection, which permits a limited axial displacement of the stent wires, but prevents a rotation of the stent wires opposite one another. The flexibility of the stent is also improved in this way. An appropriate connection may also be present at the proximal end of the stent.

Advantageously, these connection points of two spirals are found on the outer periphery, thus on the envelope of the tube-shaped stent. In this way, a disruption of the blood flow flowing through the body vessel is kept as small as possible. Advantageously, the connection sites are bent outward radially, so that in no case do they project into the lumen. In particular, in a curved course of the vessel, the ends of the stents are adapted to the curved course of the body vessel by such a design.

In order to further increase the stability of the stent, the opposed coils are combined with one another at least partially at points where the coils cross each other. A particularly advantageous connection is produced by threads of good biological compatibility, perhaps nylon threads, which are combined with one of the spirals, and which have loops at the pregiven places, through which the other loop is passed each time. Such a configuration makes possible the evolution without problem of the double spiral during the implantation. In order to avoid friction between the spirals or between the spiral and the tissue, which could lead to wear and tear of the filaments, or to tissue irritations, the spiral loops should be joined solidly with one another such that in the predetermined state, the possibility of movement of the spirals opposite one another is reduced to a minimum.

In another embodiment, the stent possesses three or more filaments. While two of the filaments are present with preferably equal pitch in the stent in the above-described way in their predetermined form, as opposed spirals, the remaining filaments that are also configured in spiral form run with a different pitch than the two opposed spirals. In this way, the third filament runs or the subsequent filaments run at least partially in the gaps opened up by the opposed double spirals. Overall, the stability of the stent is further increased and also a uniform lumen is assured for the most part over the total length of the stent.

Even if the construction of the stent from two opposed spirals is of high stability and flexibility, however, it can in some cases still be advantageous, if the stent is comprised of a double spiral which is spiraled over a part of its length in the same direction rather than in opposite directions. In this region, crossovers of the filaments with one another do not occur. Also, there is a still further increased flexibility in these segments in the stent, which, for example, is of advantage for implantation in greatly curved vessels.

In another embodiment, an improved spring effect results in the longitudinal direction of the stent. Such a stent not only has higher carrying capacity and support capacity, but it also has a higher body compatibility, particularly in the case of an implantation in a curved or flexed region of vessels.

An advantageous further development is produced, if each time, two filaments have the same type of arc-shaped segments opposed to one another at least over a part of the longitudinal extent of the stent.

Advantageously, arc-shaped segments of two filaments opposed to one another are joined together. Thus, the arc-shaped segments can be hooked with one another, or interlocked in a type of fence-like wire mesh, whereby a higher flexibility and stability of the stent is achieved. A particularly flexible, but still stable connection is produced by textile threads, which are joined rigidly with one filament, and which have loops taking up the other filament each time. Such a form of embodiment particularly facilitates manipulation when the stent is introduced in the form of longitudinally extended filaments. At the same time with such a joining, an axial mobility of the filaments opposite one another is assured, which in turn is of advantage in the region of greatly curved body vessels. Alternatively, however, for the flexible joining of the arcs under one another, a rigid connection is also possible, by means of sleeves, for example, which engage over both arcs or, by welding, soldering or gluing. Also, a combination of sleeves and other of the named fastening possibilities is conceivable. When the arcs are rigidly joined with one another, the introduction radius through the catheter can be kept particularly small.

A particularly advantageous embodiment involves, the filaments of the stent having an alternating form of arcs and spirals and are displaced relative to one another such that each time an arc crosses a spiral loop. A nearly rectangular crossover occurs thereby, whereby the stability of the stent is further improved. Preferably at the predetermined crossing point, one of the filaments has a small out-buckling, in which the corresponding filament can be taken up. The corresponding filaments engage in these places in their predetermined state, which leads to a still further increase in stability.

Appropriately, the stent is adapted in cross section in its predetermined state, to the body vessels for which it is provided. Thus it may be advantageous to provide an oval or elliptical lumen of the stent, at least in segments. Another lumen shape is necessary, for example, for the proximal part of the stent in the common carotid artery or in the bulb of the internal carotid artery, while the distal end must have a smaller diameter, since the artery cross section generally tapers here.

In another embodiment, the stent is used as a double stent. Thus only one segment of the stent has an individual tubular form of the previously described type. In a second segment, on the other hand, the stent has two lumina, which are supported each time by at least one spiral-shaped filament and which contact one another partially. Thus a double stent is constructed over at least one part of the longitudinal extent of the stent. The lumina of the two secondary stents can be constructed ovally, as described above, or, however, they may have the cross sections of two "D" pieces, which are a mirror image of one another. At their places of contact, the two secondary stents can be combined with one another, as previously described and depending on the type, by threads, which are attached to at least one of the filaments and have loops, in which the other filament is taken up each time. It is also possible that the two spirals of the double stent consist of filaments, which are arranged such that the loops, viewed in their cross section, have the form of a "figure eight", thus they cross over. In such an embodiment, an attachment of the two secondary stents with one another is not necessary.

The stents with the above-described features, are covered with a deformable membrane sheath on the outer or inner side of the double-spiral structure. The membrane is thus attached each time to the ends of the stent and is not present in the predetermined state, i.e., the expanded state of the stent under longitudinal tensile load. If the stent is pulled in length, the membrane is correspondingly extensible. As an advantageous material for such a membrane, for example, highly elastic plastic, silicone or latex are considered. Alternatively to elastically deformable membrane sheaths, however, a knitted fabric or a continuous knit can be utilized, whose meshes can be converted, upon implantation of the stent, from an introductory shape, in which the threads of the textile fabric run essentially parallel to the stent axis into an expanded form, in which the threads forming the meshes are essentially perpendicular to one another. Also, the threads of such a knitted fabric can be textured, i.e., have an expandable, spiral-shaped structure.

Particularly advantageous is the use of textile material, such as, for example, elastic fabric or polytetrafluoroethylene (PTFE), which also can be extended correspondingly. In this case, the open meshes of the fabric would be rapidly closed by thrombosis, so that also in this case a closed wall forms.

In order to prevent the textile fabric in the extended state of the stent from penetrating between the stent filaments into the inner region of the stent, metal threads that are preferably crossed are worked into the fabric structure of the textile membrane sheath, and these threads prevent the textile from entering into the region between the stent spirals.

Another advantageous possibility for providing a stent with a sheath in which, the stent has the form of a wire loop skeleton, whose individual double spiral loops are screened by fabric structures or fibers joined with the filaments opposite the vessel wall. The stent body is thus formed only in part by the filament and the rest of it is comprises fibers or fabric segments.

By screening the filaments relative to the vessel wall by means of the fabric structures/or fibers, the body compatibility of the stent is considerably increased. Such a stent thus corresponds to a stent graft. A decisive advantage of the further development of the invention according to claim 24, however, lies in the fact that, unlike the previously known wire stents with wire loops contacting one another in the region of the fabric and fiber segments, the walls of the stent unit have membrane properties, thus for example, a diffusion capability. The vessel walls can be thus be further accommodated in a path of diffusion. Additionally, a local administration of medication, is possible by coating the medication onto the novel stent wall. The danger of a possible intimal hyperplasia or another neoplastic proliferation of the vessel walls to be treated is reduced in this way. Another advantage can be seen in the fact that a reinforced accumulation of connective tissue cells or a reinforced thrombosis results in the region of the fabric or fiber segments of the stent wall. In distinction from known embolization spirals for sealing vessels according to Gianturco, the stent according to the invention specifically forms a tube provided with fibers, which leaves open the vessel volume. Based on the described cell accumulations, a biological wall is gradually formed as a consequence of the thrombogenicity of the fabric structure or of the fibers. Finally, it is possible to prepare the fibers in such a way that they can deliver medication, perhaps for producing thrombi, after successful implantation, in order to achieve a sealing of the walls of the stent body as rapidly as possible.

It is particularly advantageous, if the fabric structures and/or fibers proceeding from different spirals and/or arc segments come into contact at least partially with their free ends. In this way, the wire filament is surrounded by a sheath of fibers and/or fabric structures. Based on the described cell accumulation, this promotes the formation of a biological wall due to the thrombogenicity of the fabric structure or of the fibers. For example, aneurysms can be sealed off in this way from the normal blood flow, whereby the danger of a rupture of the aneurysm is effectively eliminated, or at least is considerably reduced. The treatment of aneurysms is particularly advantageous when these are present in the abdominal aorta in the infrarenal segment, but also for small intracranial aneurysms.

The stent can be produced without the use of foreign adhesives, which are of doubtful stability and body compatibility, so that at least one filament including the fabric structures or fibers is sheathed and/or enveloped. This sheathing or enveloping can be produced by means of another textile or thread. An additional fastening of the fabric structures or fibers is not necessary.

In another embodiment of the invention, the fastening of the fabric structures or splitting fibers can be produced simply by interweaving a filament from several filaments as the filament, whereby the fabric structures and fibers are maintained within the interweavings of the individual filaments. The fabric structures and/or fibers are thus passed through openings, which are present between the filament parts interwoven with one another. Instead of this, it is also possible to provide openings in a filament, through which the fabric structures and/or fibers are drawn. At least with such a form of embodiment, the filament appropriately has a rectangular cross section. Also, in the case of this embodiment, the use of additional adhesives or other fastening means for the tissue structures or fibers is not necessary.

Appropriately, fabric structures and/or fibers extending radially from one filament are of different lengths in segments and/or according to radial direction, corresponding to the requirements of the respective body vessel.

In a particularly advantageous configuration, the fabric structures and/or the fibers are attached to the filaments such that their free ends contact each other, at least approximately, with the formation of a wavy line-shaped boundary line. In the transition to the predetermined state, a particularly advantageous adaptation of the sheath of fabric structures and/or fibers to the spiral structure is thus assured.

A particularly compact and rigid stent sheath is produced by overlapping the fabric structures and/or the fibers, at least partially, between the individual adjacent spirals and/or arc segments formed by the filaments.

The fabric structure of the stent can be produced from a textile as well as a metal in order to produce membrane segments capable of diffusion. When textile fabrics are used, the membrane segments have smaller pores and when metal fabrics are used, they have larger pores. In the case of small-pore fabric segments, thrombosis is produced and the organization of the introduced structures is accelerated. Metal fabric structures, on the other hand, have a higher crosswise stability. However, a combination of metal and textile fabric structures can also be meaningful.

The crosswise stability of such a stent can also be increased by cutting the fabric structures in the form of a fringe, at least in segments. The fabric structures can be overlapped and interlocked in a reinforcing and compacting manner with an appropriate length of fringe.

The same objective may also be achieved in that the fabric structures are provided with an adhesive agent, preferably a Velcro® seal, in order to join the fabric structures overlapping with one another. The use of appropriate Velcro® strip seals also assures that the longitudinally extended filaments achieve their spiral shapes at the site of implantation. This adhesive effect can also be achieved by arranging thin fabric strips, which have alternating "hooks and eyes" according to a type of Velcro® seal strip on the filament.

According to patent claim 35, due to the fact that the cross section of the fabric structures used decreases outwardly with increasing distance from the respective filament, it is assured that the stent also has an essentially uniform outer diameter even in the region of the overlappings. Appropriately, the fabric structure consists of and/or the fibers consist of an elastic material. In this way, it is achieved that the fibers are aligned automatically to their specified position extending continuously radially from the filament after passage through the catheter. The fibers can be joined with the filament by means of a mechanically producible suture. This makes possible a particularly simple production of such stents.

In order to seal the stent in an optimal way relative to the body vessel, it is appropriate to dimension the lengths of the fibers, e.g., in connection with treatment of aneurysms, such that the interweaving of these fibers preferably projects into the corresponding vessel outpocketing and in this way a reinforced thrombosis occurs in the region of the vessel outpocketing. It is also conceivable that the fibers project preferably radially into the inside of the stent, in order to form an anastomosis with a stent lying approximately thereunder. The connection to a second inserted stent is better sealed with this further embodiment of the invention.

The implantation of a stent and its positionally-correct placement can be facilitated by providing at least one filament with special markings, which facilitate the observation of the stent by remote fluoroscopy. However, other diagnostic observation methods are also conceivable, such as, e.g., magnetic resonance tomography or ultrasound.

As an alternative to the above-named forms of embodiment, in which the inner region of the stent is enclosed by a double-spiral structure, the stent according to claim 38 has a double-spiral structure in which essentially parallelly running filament wires at predetermined intervals form coiled loops opposed to one another each time along the longitudinal extent of the stent. The outer radius of the stent is determined by the radii of the loops. During the implantation, the loops are laid out in the stretched state on the otherwise longitudinally extended stent body. At the site of implantation, the loops preferably comprise superelastic or thermo-memory material are then aligned relative to their implantation. Like the previously described forms of embodiment, this stent may also be surrounded by a membrane of elastic material and the filaments of the stent can be joined to one another again by means of sleeves.

It is particularly advantageous if the stent is implanted with an implantation device. First, a catheter is inserted into the body vessel to be treated. The catheter is dimensioned such that both the stent as well as a special pushing device arrangement comprised of two pushing devices can be inserted into the body vessel. The pushing-device arrangement consists of an outer and an inner pushing device. The outer pushing device has a diameter that corresponds to the inner diameter of the introduction catheter, and also has approximately the same outer circumference as the stent in its introductory state, thus approximately the total circumference of the longitudinally extended filaments that are inserted. By means of this pushing device, the stent is advanced through the catheter up to its predetermined site in the body vessel, where it assumes its predetermined state, i.e., with the double-spiral structure of the filaments. A borehole extends axially through the outer pushing device, through which a second, inner pushing device is displaced. The latter, which is a thin pushing device produced, however, of a rigid material, e.g., Nitinol®, has means at its distal end, with which it can be joined with the distal end of the stent.

By introducing the stent in its extended state into a body vessel, the latter is advanced in the catheter by means of the outer pushing device. When the stent exits from the catheter, i.e., when several loops of the double spiral have already formed in the vessel, the stent is held in the vessel coaxially by means of the inner pushing device. A springing back or a springing forward of the stent in the body vessel can be avoided in this way. An exact placement of the distal stent end in the body vessel is also possible in this way. The distal stent end is also held in its place by the thin pushing device, if the catheter is pulled back and/or the stent is advanced by the outer pushing device. Alternatively, the stent can also be pulled into the body vessel, after placement of the catheter, by means of the inner pushing device, which is joined with the distal stent tip. In this way, the stent is extended axially during the implantation procedure, whereby the friction between filaments and catheter wall is reduced. Only when the stent is completely introduced into the body vessel is the thin pushing device released from the stent tip. It is possible in principle to place the stent in the body vessel only by means of one of the pushing devices; however, the combination of the two pushing devices makes possible a particularly exact and disturbance-free implantation and placement of the stent in the body vessel.

A screw thread serves as an advantageous joining means between the inner pushing device and the stent, which is arranged preferably at the distal end of the inner pushing device, and which engages in the corresponding fastening means of the stent, i.e., one of the loops formed at the distal end of the stent by the two spirals of the double spiral. Of course, the stent can also have appropriate fastening means at its distal end, i.e., in the form of a threaded borehole adapted to the thread of the pushing device. Alternatively, hooks that correspond to one another and are arranged on the tip of the stent and the pushing device may also be used. It is also possible to join the stent and the pushing device with one another by a special soldering process, which can be triggered in the body by an appropriate electrical current. Such a principle is already applied in the case of embolization coils.

In a number of treatments, it has turned out that the lumen of a body vessel remains open after some time, even without the support of a stent. It is thus appropriate to provide devices, by means of which, the stent can be removed again from the vessel after some time. For this reason, the stent can be joined in a detachable manner with the outer pushing device. As a joining material, a threaded screw connection can be used again, or, possibly a holding clip, which is arranged at the proximal end of the stent and which can be grasped with the corresponding hook of the pushing device. It is thus not necessary to leave the pushing device in the body during the entire time of stent placement. After a predetermined time, the stent can be withdrawn from the body vessel through the catheter by the outer pushing device.

If the filaments of the stent are comprised of a material with thermo-memory properties, the latter should be implanted by a catheter filled with cooling liquid, in order to avoid the circumstance that the stent wire springs into the more voluminous spiral shape inside the catheter and thus prevents the implantation, due to the friction between the stent wire and the inner wall of the catheter.

As an alternative to the means named above, which involves two pushing devices, for the implantation of the stent according to the invention, in which a pushing device that can be introduced into the body vessel by means of a catheter is provided on its distal end with a support means for supporting the stent inside the catheter.

As a particularly advantageous support means, a fork arranged at the distal end of the pushing device is provided, which engages the filaments with its tines at the crossover points or connections or at the sleeves joining the filaments together during the implantation, and thus makes possible a particularly secure guidance of the stent in a positionally-correct implantation in the body vessel.

In another advantageous further embodiment of the invention, a forceps device is provided as a proximal support means, by means of which the filaments or the sleeves joining these filaments with one another are rigidly grasped during the implantation of the stent, but after an axial activation of the catheter, are detached from the latter. In this way, the stent can be withdrawn in the direction of the catheter, in case an erroneous placement should occur.

In another advantageous further embodiment of the invention, the support means of the pushing device are shaped like a hook and the stent has a sleeve joining the filaments together at its distal end, in which a notch is impressed, which can be joined with the hook in a form-fitting manner and is axially stationary inside the catheter. This form of embodiment is also characterized by a particularly reliable guidance of the stent during implantation.

BRIEF DESCRIPTION OF THE DRAWINGS

The invention will be explained below on the basis of several embodiments shown schematically in the attached drawing. In the views, which are not shown to scale:

FIG. 16 shows a filament of individual wires with a twisted fiber structure, twisted together, FIG. 17 shows an ensheathed filament with enclosed fiber structure, FIG. 18 shows in an excerpted view, a touching or "kissing" stent in longitudinal section, FIG. 19 shows the "kissing" stent according to FIG. 18 with inner fibrillation at the distal end in cross section, FIG. 20 shows a filament joined with a Velcro® strip in a cross section, FIG. 21 shows an excerpted view of a longitudinal section through another "kissing" stent, FIG. 22 shows the "kissing" stent according to FIG. 21 in cross section, FIG. 31 shows the distal end of a stent with an implantation device in yet another form of embodiment in a lateral view, and FIG. 32 shows the stent and the implantation device of FIG. 30 in a top view.

Figures 1, 2:
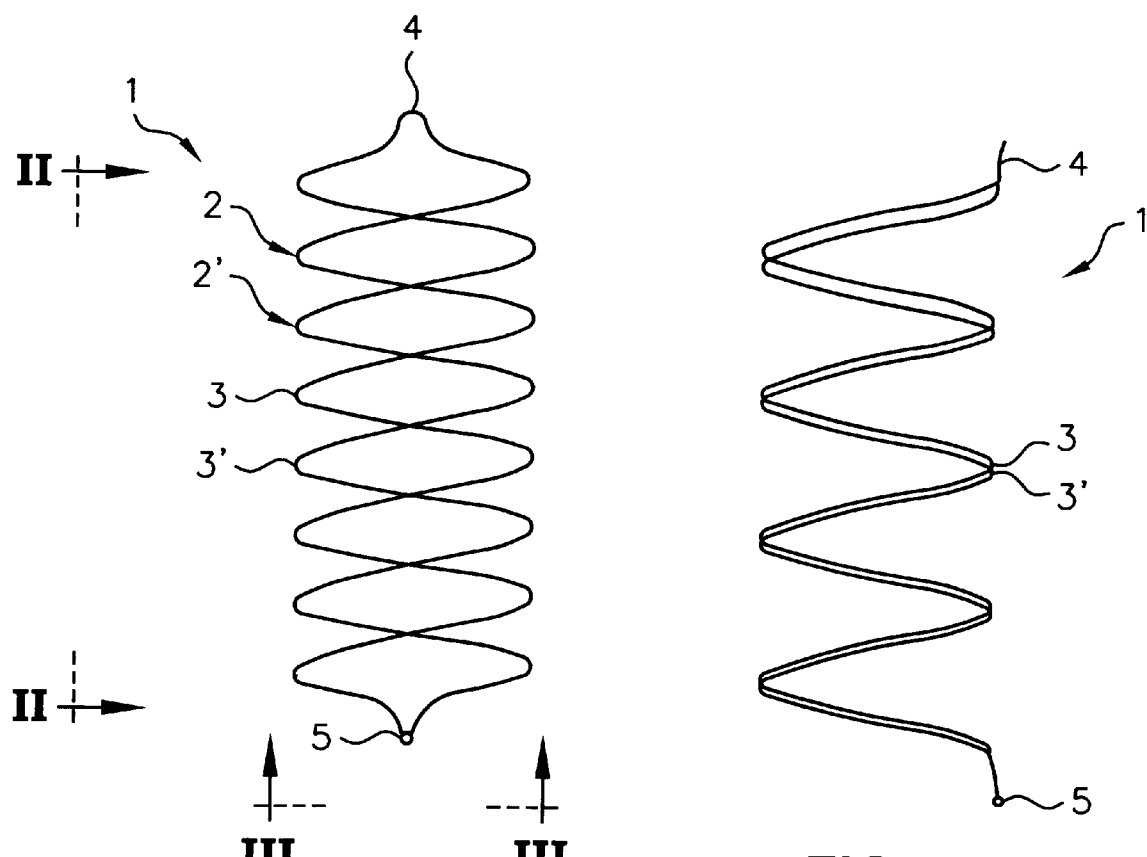
FIG. 1 shows a stent with two opposed spiral filaments in its predetermined state in a top view.
FIG. 2 shows the stent in a view according to arrow II in FIG. 1.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 3:
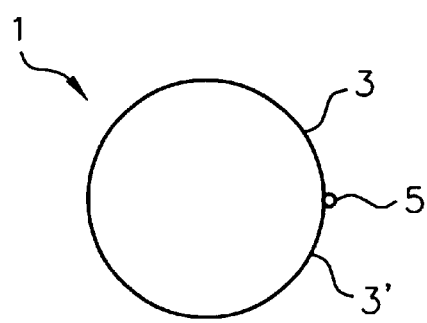
FIG. 3 shows the stent in a view according to arrow III in FIG. 1.

Stent 1 shown in FIGS. 1 to 3 is comprised of two filaments 2, 2', which are wound into two opposed spirals 3, 3'. At the distal end of stent 1, the two spirals 3, 3' transform into a loop 4, which joins together the two filaments 2, 2', one into the other. The filaments 2, 2' are thus parts of a single wire. The two filaments 2, 2' are joined together with a connection means, i.e., a sleeve 5 engaging over the two filaments 2, 2' at the proximal end of stent 1. Instead of the sleeve, however, the ends may also be welded, soldered, or bonded. Both loop 4 at the distal end of stent 1 as well as sleeve 5 at the proximal end are arranged radially on the outer side relative to the longitudinal extent of stent 1. In this way, a uniform lumen is kept open over the entire length of stent 1.

Figures 4, 5:
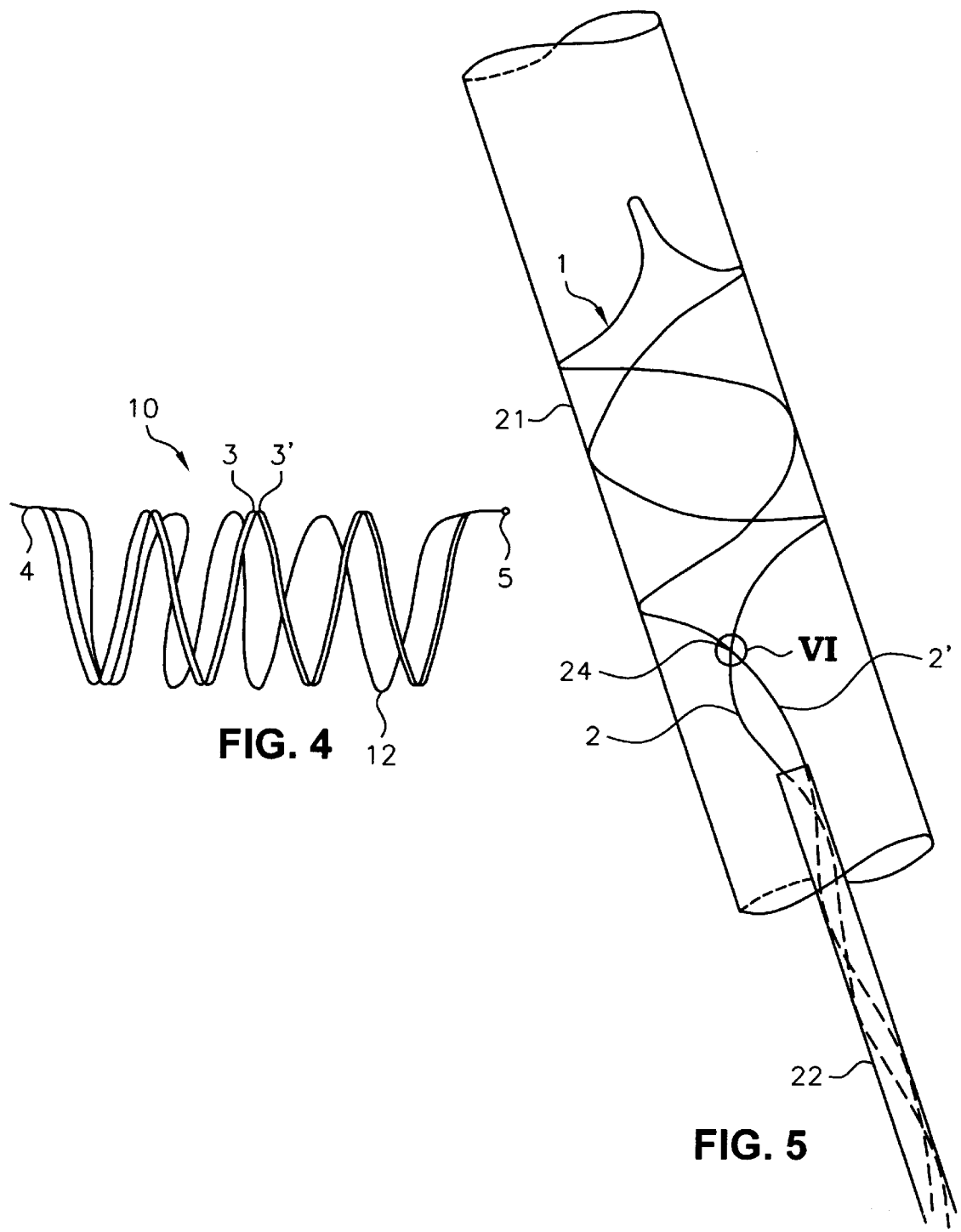
FIG. 4 shows a stent comprised of three spiral-shaped filaments in a view similar to FIG. 2.
FIG. 5 shows a stent partially in its longitudinally extended implanted form in a catheter and partially in its predetermined state in a body vessel.

FIG. 4 shows a stent 10, which is constructed of three spiral-shaped filaments 2, 2', 12. Filaments 3, 3 essentially have the same pitch and form the double-spiral structure known from FIGS. 1 to 3. Filament 12 has, at least in segments, a pitch that is modified relative to filaments 3, 3. In this way, filament 12 also assures a vessel support in the region of gaps in the double-spiral structure comprised of filaments 3, 3.

FIG. 5 shows a stent 1 during its implantation in a body vessel 21. Thus stent 1 with its filaments 3, 3 is advanced through a catheter 22 in a way that will be described in more detail below, by means of a pushing device not shown here. Filaments 3, 3, as desired, are comprised of thermo-memory wire, such as Nitinol®, or they are comprised of longitudinally extended flexible wire of highly elastic plastic. Filaments 3, 3 of stent 1 project within the body vessel 21 to be treated at the proximal end from catheter 22 and spring into the desired double-spiral form based on the named thermo-memory property or the elasticity.

When a thermo-memory wire is used, catheter 22 should be rinsed with a cooled physiological saline solution in order to prevent filaments 2, 2', which are already inside catheter 22, from springing into the spiral form. If this is note done, the friction force preventing the advance of filaments 2, 2' within catheter 22 would be considerably increased due to the bulky filaments 2, 2'. For this purpose, an inlet valve for the physiological saline solution can be provided at the proximal end of catheter 22 and a lock valve can also be arranged at the distal end of catheter 22, which in fact allows the discharge of the physiological saline solution in an unhindered manner, but, on the other hand, prevents the entry of warm body fluid.

Figure 6:
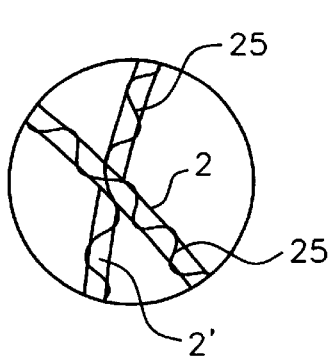
FIG. 6 shows in an excerpt VI from FIG. 5 an enlarged crossover region of two filaments.

In order to increase the stability of stent 1 in its predetermined state, filaments 2, 2' are provided with an arrangement of threads 25 at least in the region of crossover points 24. In this example of embodiment, threads 25 are coiled in a spiral around both spirals of filaments 2, 2'. In crossover region 24, thread 25 on one of filaments 2, 2' is detached from filaments 2, 2', such that a distance arises between thread 25 and filaments 2, 2', which is sufficient for taking up the other filament 2, 2'. In the construction of the predetermined double-spiral structure of stent 1 from the longitudinally stretched implantation structure, filaments 2, 2' forming the spirals are purposely mutually twisted. For this reason, the joining of the two filaments 2, 2' in crossover region 24 must be designed such that the two filaments 2, 2' can be mutually twisted. With the joining as shown in FIG. 6, an effective radial stability of the stent is obtained, and simultaneously the two filaments 2, 2' can be mutually twisted. Also, filaments 2, 2' have a certain axial mobility relative to one another. This is particularly of advantage in the case of implantation of the stent in greatly curved body vessels.

Figure 7:
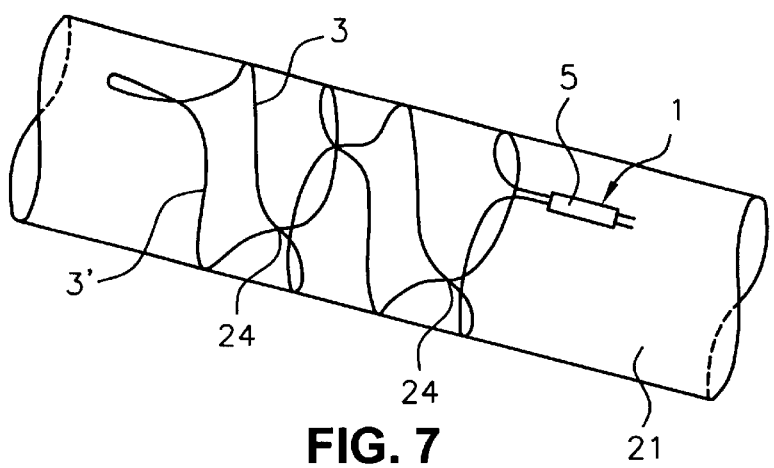
FIG. 7 shows another stent in the implanted state.

In the case of the form of embodiment shown in FIG. 7, the individual spiral loops of spirals 3, 3' are bent in such a way that they run somewhat at right angles to each other at their crossover points 24. Both spirals 3, 3' are thus applied to the inner walls of a body vessel 21. One of the spirals 3, 3' can have a bent-up part only in the region of crossover points 24, in which the other spiral 3, 3' is taken up, as this is shown, e.g., in FIG. 25.

Figure 8:
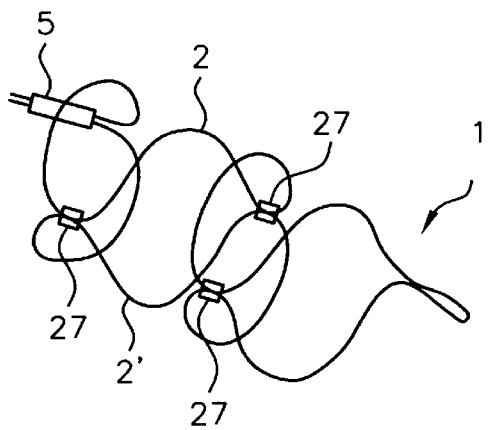
FIG. 8 shows a stent with arc-shaped filament segments in its predetermined state, whereby the filament segments are joined with one another by connection means.

In the form of embodiment according to FIG. 8, spirals 3, 3' in the region of their crossover points are joined together by suitable connection means, e.g., sleeves 27 engaging over both filaments 2, 2'. However, thread connections are also considered as joining means, as they are shown in FIG. 6.

Figure 9:
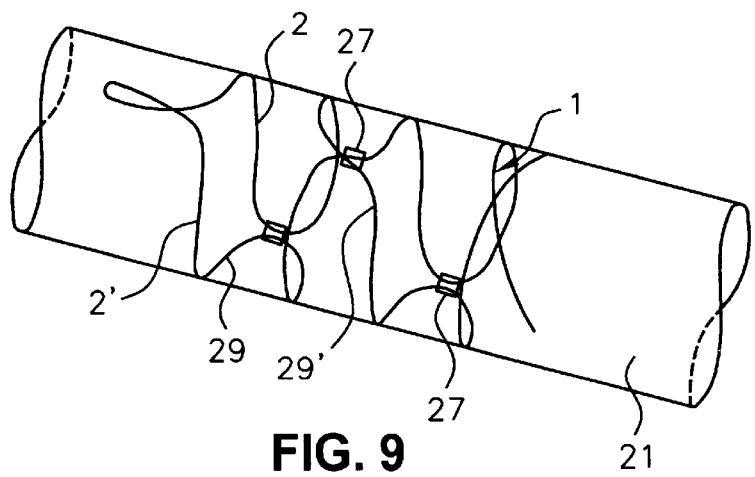
FIG. 9 shows a stent in its predetermined state with arc-shaped filament segments.

In the form of embodiment according to FIG. 9, the distal segment of stent 1, instead of a double spiral, has a structure of opposed arc segments 29, 29', running radially at the inner wall of body vessel 21. Adjacent arc segments 29, 29' of a filament 2, 2' are thus displaced relative to one another by approximately 180° in the peripheral direction, whereby a particularly stable form of stent 1 is assured. For further stabilization of the stent, filaments 2, 2' are joined together by means of sleeve 27 in the region where arc segments 29, 29' approach each other maximally. Of course, suitable sleeves 27 may also be arranged in crossover region 24 of two filaments 2, 2' of a stent of the type shown in FIG. 7 or FIG. 8 and the filaments can be joined with each other also in another way, e.g., by welding, gluing, or soldering, or by a combination of welding, soldering or gluing with the sleeve. Depending on the application, the wires can be joined so that they can rotate opposite one another or they can be joined together rigidly by the named connection means.

Figure 10:
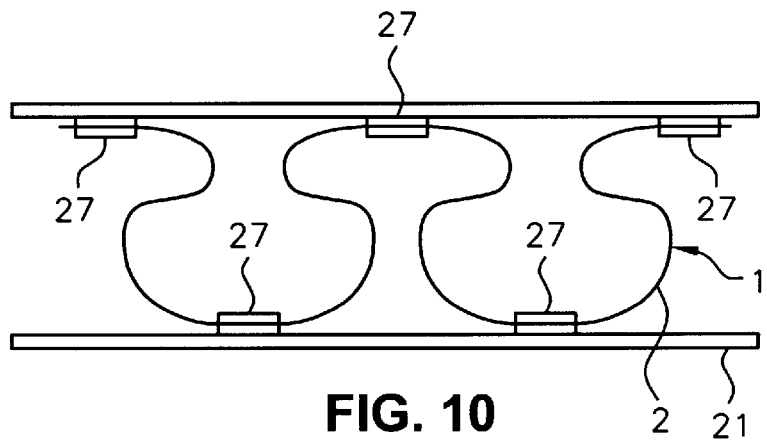
FIG. 10 shows the stent from FIG. 9 in a lateral view.

It is shown in FIG. 10 that—seen from a lateral view—filaments 2, 2' of the stent according to FIG. 9 each have an approximately "S"-shaped course between two points of maximum approach of arc segments 29, 29'—which are indicated in FIG. 10 by sleeve 27 connecting the filaments together. Unlike the stent structure previously known from WO 94/03127, with filaments that run parallel to one another between each of the two connecting segments, the stent structure in this configuration has a particularly high flexibility. Also, the stent according to FIG. 7 or the stent according to FIG. 8 can be shaped in this form of embodiment with—seen in a lateral view—essentially "S"-shaped running filaments 2, 2' between every two adjacent crossover points 24. Based on the "S"-shaped course of the filament, the stent has an extraordinarily high flexibility and, in particular, the vessel with the implanted stent is compressible thereby. A pulse wave can better pass over such a stent than in a stent with filaments running perpendicular to the longitudinal axis of the stent.

Figure 11:
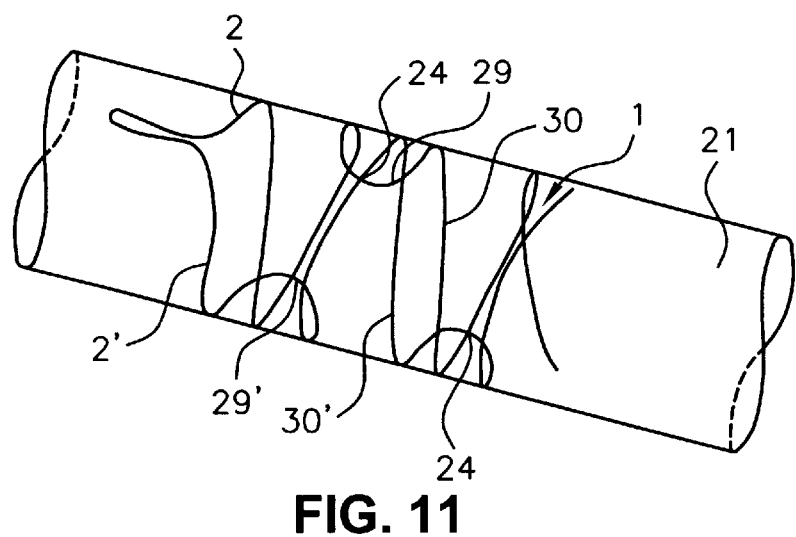
FIG. 11 shows a stent in another form of embodiment in its predetermined state, in which the filaments have an alternating form of arcs and spirals each time.

In the form of embodiment according to FIG. 11, filaments 2, 2' of a stent 1 have an alternating sequence of arc segments 29, 29' and spiral loops 30, 30'. On both filaments 2, 2', the sequences are displaced such that each time a spiral loop 30, 30' crosses an arc segment 29, 29' in the region of crossover point 24 of the two filaments 2, 2'.

Figure 12A:
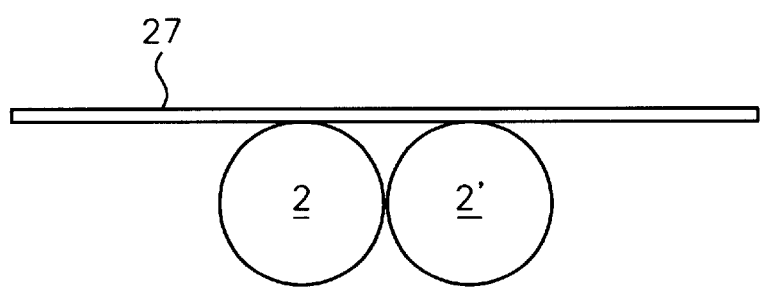
FIG. 12a shows a sleeve comprised of a material with thermo-memory property in the state prior to joining of two filaments.
Figure 12B:
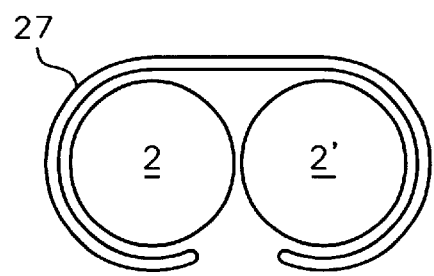
FIG. 12b shows the sleeve of FIG. 12a in its predetermined state surrounding two filaments.

A preferred form of embodiment of a sleeve 27 joining two filaments 2, 2' each time is shown in FIG. 12a and b. Sleeve 27 comprises a material with thermo-memory property and is shown in the state prior to joining the filaments in FIG. 12a, thus as an essentially rectangular and flat-running segment. After reaching a predetermined thermo-memory transition temperature, sleeve 27 bends essentially into a U-shape and encloses filaments 2, 2', whereby a particularly stable connection is produced, essentially stopping the rotation of filament wires 2, 2' relative to one another. Sleeves 27 may be of different lengths, adapted to the respective requirements. Thus the number of spiral loops 3, 3' per unit length of the stent can be reduced in regions in which only a small load of the stent body exists in a simple way, by using an appropriately lengthwise extended sleeve in the crossover region for joining the two filaments 2, 2'. On the other hand, short sleeves are recommended in the region of the stent ends, since there the stent load is particularly high and a high spiral density is desirable.

Figure 13:
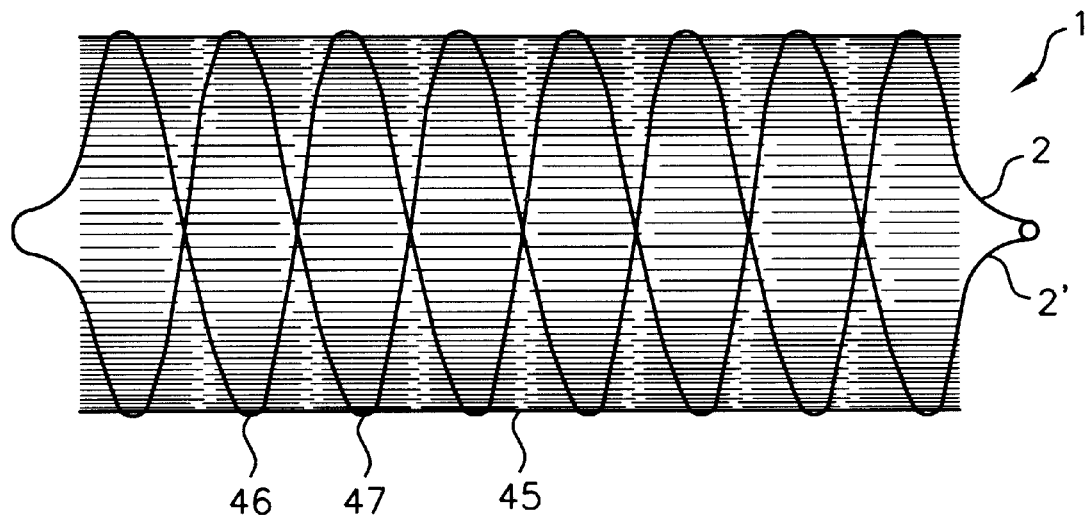
FIG. 13 shows a stent provided with an envelope of a fiber structure in a view similar to FIG. 1.
Figure 14:
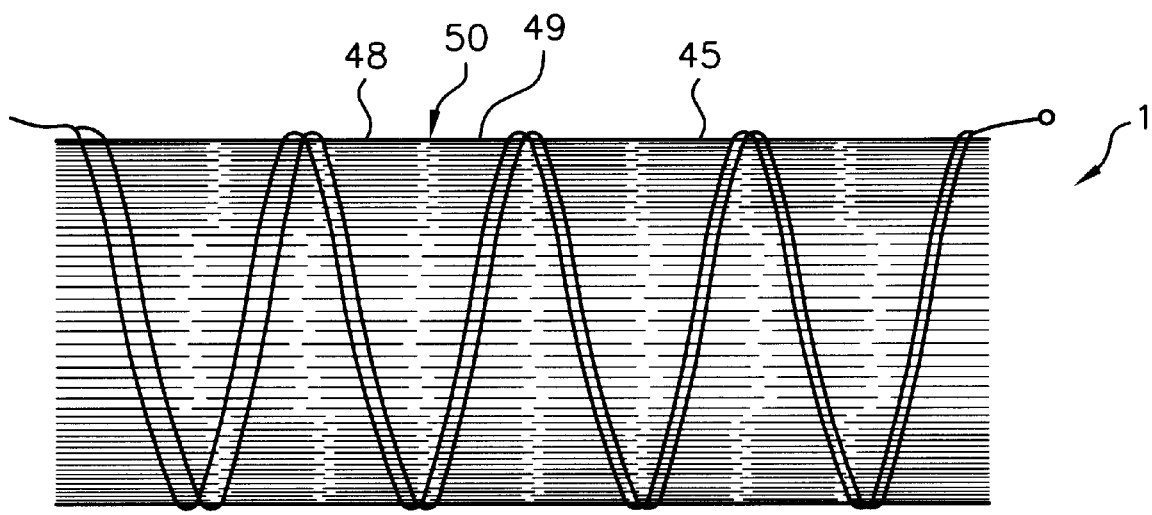
FIG. 14 shows the stent of FIG. 13 in a view similar to FIG. 2, FIGS. 15A–15D show different embodiment possibilities of the overlapping regions of the fibers proceeding from adjacent filaments for the stent according to FIG. 13.

In the form of embodiment shown in FIGS. 13 and 14, filaments 2, 2' of stent 1 are joined with a fabric or metal structure 45 such that a tube-shaped sheathing of stent 1 results. The sheathing formed by the fabric or metal structure 45 is capable of diffusion, due to its porosity; on the other hand, with the use of textile fabric parts, the sheathing is very finely porous; and still on the other hand, with the use of metal fabrics, it is shaped with very large pores. The decision of whether to use a fabric or a metal structure depends on the desired stiffness of stent 1 and the required diffusion properties.

The fibers or fabric parts proceeding from adjacent spiral loops 46, 47 form boundaries with one another in an overlapping region 50 between adjacent spiral loops 46, 47. The individual fabric parts and/or fibers can be bound to one another in different ways, as FIG. 15 shows.

In FIG. 15, in excerpts, the overlapping region 50 between fibers or fabric parts of fabric structure 45 proceeding from adjacent spiral loops 46, 47 is shown on the example of fibers 48, 49 bounding one another in different structural forms a) to d). The densest and most rigid connection of the fabric parts or fibers with one another consists of an overlapping of fibers 48, 49 proceeding from adjacent spiral loops 46, 47. FIG. 15a and 15b show this type of joining. While in the form of embodiment according to FIG. 15a, the fiber density of fabric structure 45 remains constant out over the stent, there results in the form of embodiment according to FIG. 15b zones of greater density and thus of greater thickness of fabric structure 45 in region 50 where fibers 48 and 49 overlap.

Figure 15A:
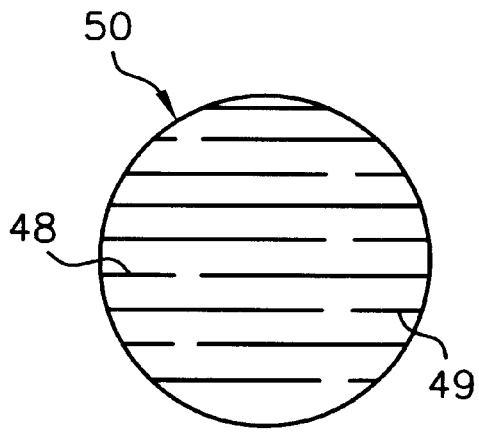
Figure 15B:
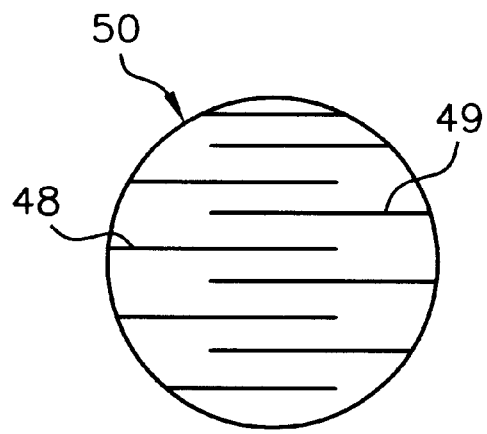
Figure 15C:
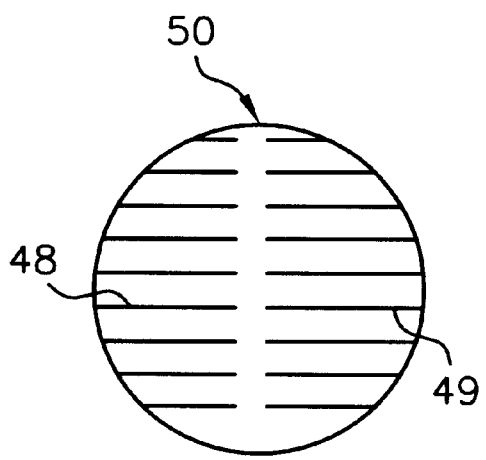
Figure 15D:
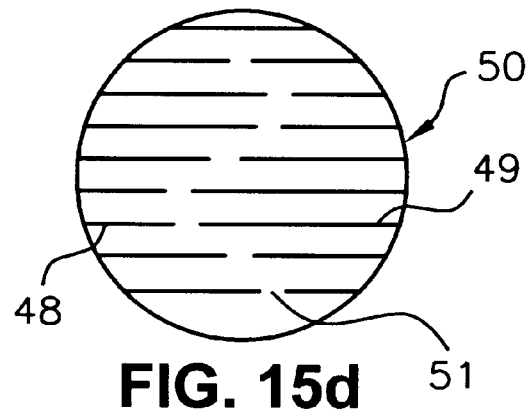

Another form of embodiment is shown in FIG. 15c, in which the fibers are not overlapping, but come into contact only at their ends, whereby a circular transition zone is formed over the outer periphery of stent 1. A stent that is shaped in this way has a smaller stiffness and strength when compared with the structural forms according to 15a and 15b, but requires a considerably smaller expenditure of material and is thus clearly lighter in weight than the above-named forms of embodiment. Also, the introduction catheter can have a smaller lumen. In the form of embodiment according to FIG. 15d, finally, there is also present no overlapping of fibers 48, 49, but fibers 48, 49 are shaped such that their ends form a wavy-shaped transition line 51 in transition region 50.

FIGS. 16 and 17 show different possibilities of joining a fabric structure with filaments 2, 2'. According to FIG. 16, filament 2 is provided with fibers 48 extending radially from filament 2. Fibers 48 for the most part are comprised of DACRON® or TEFLON® material and may have different lengths in segments or according to preferred direction. In FIG. 16, filament 2 is produced from filament parts 55, 55' twisted with one another. Filament parts 55, 55' are also comprised of thermo-memory wire or highly elastic plastic. DACRON® fibers 48 are held between the individual filament parts 55, 55' by means of twisting these filament parts 55, 55'. In this form of embodiment, no foreign adhesives with doubtful or limited stability are required.

In the form of embodiment shown in FIG. 17, a filament 2 is wrapped by a sheath 56. This sheath 56 can also be comprised of a textile or metal fabric structure. An auxiliary thread or auxiliary wire may also be involved and may be attached to filament 2 approximately in the way shown in FIG. 6 by means of a thread 25. Also in this form of embodiment, sheath 56 is wound around filament 2 so that it encloses fibers 48 extending radially from the filament.

Fibers 48 extending from a filament 2 in the examples of embodiment according to FIGS. 16 and 17 also serve for forming a sheath between the individual spiral loops 30, 30' of stent 1. The interwoven piece formed of individual fibers 48, however, may be utilized, specifically for producing thrombosis, for example within a diseased outpocketing, i.e., an aneurysm. According to another embodiment, fibers 48 can also project specifically inside stent 1, in order to accelerate a desired vessel occlusion.

FIGS. 18 and 19 show a stent for a special method of treatment for vessel disorders in the region of vessel branchings. The so-called "kissing" stent method is used successfully for this. A principal stent 1 with larger diameter is implanted in branching vessel 60 and then on the distal side other auxiliary stents 61, 61' are inserted through the branching vessel distally of stent 1, which has been implanted first. In the case of a pathological abdominal aorta with an aneurysm, auxiliary stents 61, 61' are inserted through the femoral artery of the lumen distal to the already implanted principal stent 1. Up until now, this procedure has been problematical, since in the region of the branching of the two distally inserted auxiliary stents 61, 61', a leakage has occurred, since the subsequently distally inserted auxiliary stents 61, 61' did not fill up the entire lumen of the originally implanted principal stent 1. By employing the segmental arrangement of fibers 48 projecting inwardly according to FIG. 19 at the distal end of principal stent 1, the described leakage can be effectively eliminated by an accelerated thrombosis occurring within the leakage zones. Fibers 48, however, may also be arranged on auxiliary stents 61, 61' and point radially outwardly. Depending on the packing density and radial extent of fibers 48, it is possible in this case under certain circumstances, to completely eliminate principal stent 1. An effective thrombosis is then produced directly between the wall of body vessel 60 and auxiliary stents 61, 61'. Of course, instead of fibers 48, another dense covering, i.e., a fabric structure may also be used. The two auxiliary stents 61, 61' can thus also be comprised of a stent 35 formed of a double-spiral structure and have the cross section of a "figure eight" in the region in which they are inserted into the principal stent. This is shown in FIG. 19.

According to FIG. 20, the fabric or metal structure 45 joined with filament 2 can be joined with a Velcro® strip 63.

This is used for forming Velcro® seals 64 in the region of overlapping of fabric or metal structures 45 proceeding from spirals adjacent to one another. In this way, an improved crosswise rigidity of stent 1 is obtained. In addition, fabric structure 45 can be outwardly tapered with increasing distance from filament 2, in order to assure a uniform outer contour of stent 1, in contrast to the representation in FIG. 20, which is not to scale. The rectangular cross section of the stent filaments shown in FIG. 20 makes possible a particularly solid connection of the Velcro seal with the filament. A rectangular filament cross section generally assures a more stable attachment of the sheath and/or fiber material to the stent filaments. However, filaments with a "D"-shaped cross section may also be used as an alternative to the rectangular filament cross section shown in FIG. 20. In order to produce a particularly high tightness of the Velcro® seal 64, after implantation has been produced, a balloon catheter should be introduced into the stent, and this should be placed in its expanded state for a brief time in the region of Velcro® seal 64, whereby Velcro strips 63 are pressed against each other.

Complementary to FIGS. 18 and 19, another design of the invention for conducting the "kissing" stent method is shown in FIGS. 21 and 22. FIG. 21 shows a longitudinal section through an infrarenal aortic aneurysm 62, which reaches up to the bifurcation. Also in this configuration, two secondary stents 61, 61' are provided in the region of the vessel branching, and these stents coincide with the vessel branching. Instead of the principal stent 1 shown in FIG. 18, in the embodiment according to FIGS. 21 and 22, only compact ring stents 67, 68, 69 are provided, which only have a small longitudinal extent. The cross section in the region of the neck of the aneurysm shown in FIG. 22 shows the compact ring stent 67 in an enlarged view when compared with FIG. 21. Fibers extending from compact ring stent 67 on one side project radially inside the vessel lumen and are joined with the secondary stents 61, 61', and on the other side they project out radially on the outside over the outer periphery of compact ring stent 67 and conform to the wall of body vessel 60 in the region in front of the aneurysm. In this way both a leakage between the two auxiliary stents 61, 61' between each other as well as relative to the wall of the aorta in the region of aneurysm 62 are avoided. The function of compact ring stents 68, 69 is to be understood as analogous to the function of compact ring stent 67. In an advantageous configuration, the secondary stents 61, 61' that are introduced also have an oval or D-shaped cross section, in order to achieve a better filling of the aortic lumen, and thus provide an improved sealing effect. In this way, the risk of an aortic rupture at the aneurysm is effectively prevented.

Figure 23:
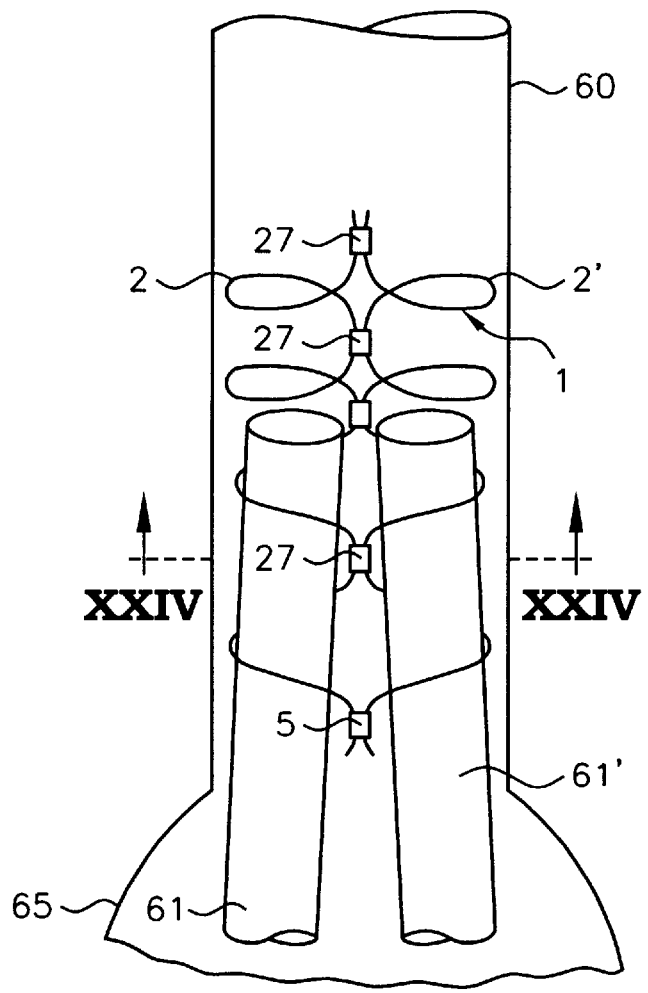
FIG. 23 shows a "kissing" stent in another form of embodiment.
Figure 24:
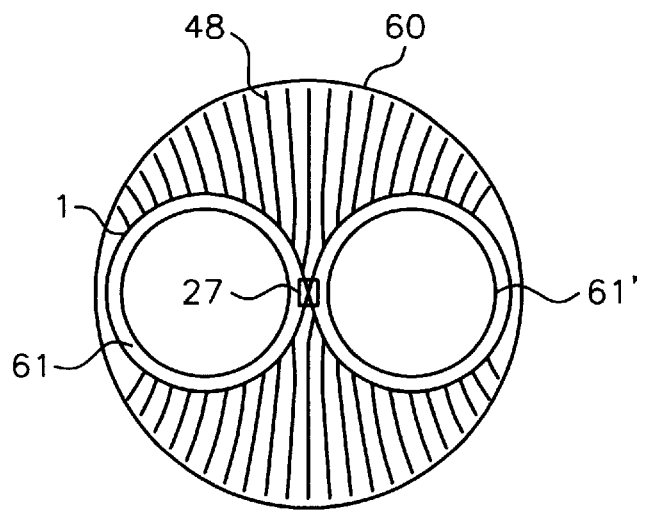
FIG. 24 shows the "kissing" stent according to FIG. 23 in cross section along cutting line XXIV–XXIV in FIG. 23.

Still another possibility for producing a "kissing" stent by means of the double-spiral stent, is shown in FIGS. 23 and 24. The "kissing" stent is again illustrated in FIG. 23 in its implantation state in a body vessel 60 in the region of an aneurysm 65. In the case of this "kissing" stent, principal stent 1 has one lumen in its distal segment and two lumina, on the other hand, in its proximal segment, in which secondary stents 61, 61' are inserted during implantation as illustrated only segmentally in FIG. 23. The two filaments of principal stent 1 are formed in this proximal segment in such a way that stent 1 has the shape of a "figure eight" in cross section—as shown in FIG. 24. In this way, a very reliable and stable connection between principal stent 1 and secondary stents 61, 61' is created. Alternatively to the "figure eight" structure, stent 1 may also be present in the form of two opposed individual spirals lying next to one another and contacting each other at points, or at least approaching each other, in the proximal segment of the stent. In order to obtain a stability corresponding to that of the form of embodiment according to FIG. 23, the opposed spirals in this case, of course, must be joined with each other at their points of contact by means of sleeves 27 or threads 25 shown in FIG. 6.

As shown in FIG. 24, there is the possibility also in the case of these "kissing" stents to obtain an accelerated thrombosis by means of fibers 48 and/or fabric structures projecting radially from the filaments of principal stent 1 and/or secondary stents 61, 61' in the direction onto the wall of body vessel 60. In order to better utilize the lumen of body vessel 60, the two lumina of the proximal segment of stent 1 may also have an oval cross section each time, instead of the circular cross section shown in FIG. 24.

Figure 25:
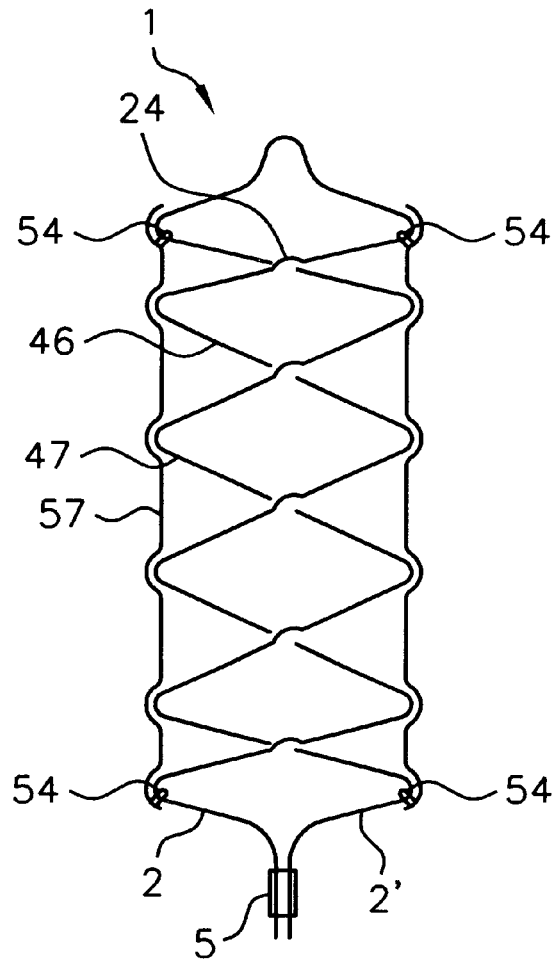
FIG. 25 shows a stent provided with a sheathing of an elastically deformable material, in a view similar to FIG. 1.

In FIG. 25, stent 1 has a membrane-type sheath 57, which encloses stent 1 radially on the outside and which is joined with filaments 2, 2' by means of sutures 54, instead of a fiber or fabric structure joining filaments 2, 2'. Sutures 54 should preferably be attached to the ends of stent 1, but they may also be arranged in other regions of the stent body.

Filaments 2, 2' joined with the proximal end of stent 1 by means of a sleeve 5 form opposed spirals, whose individual spiral loops 46, 47 in FIG. 25 have different pitches over the longitudinal extent of stent 1. Sheath 57 is comprised of a textile knitted piece, but may also be formed of a body-compatible highly elastic material, preferably plastic, latex or silicone. Thus sheath 57, on the one hand, closely conforms to spiral loops 46, 47 of filaments 2, 2, so that the stent is implanted in its predetermined state in the body vessel in a nearly radially rigid position, and on the other hand, sheath 57 has a lumen in the region between adjacent spiral loops 46, 47, which at least approximately corresponds to the lumen of spiral loops 46, 47. Sheath 57 also encloses a bent-out part of one of the two filament wires 2, 2' shown in the example of embodiment according to FIG. 25, in the region of crossover 24, which does not adversely affect the stability.

Figure 26:
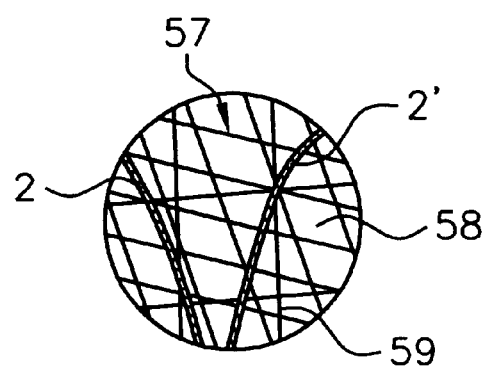
FIG. 26 shows the sheathing of the stent of FIG. 25 in a enlarged excerpt.

FIG. 26 shows sheath 57 of stent 1 from FIG. 25 in an enlarged segment, in its predetermined implantation state. In this state, stitches 58 run in rhomboidal shape over the outer periphery of the stent body formed from filaments 2. Depending on the degree of expansion of the stent each time in its implanted position, the angle enclosed by the sides of the rhomboidal-shaped stitches 58 can be configured differently up to an approximate rectangular shape of stitches 58. In the extended state of the stent, on the other hand, the threads forming stitches 58 of sheath 57 run approximately parallel to one another. In order to prevent a penetration of the textile threads of sheath 57 into the intermediate region between spiral loops 3 of the filaments in the implantation state, sheath 57 is additionally provided with reinforcement threads 59 preferably comprised of metal, which are worked into sheath 57 also as stitches in the example of embodiment according to FIG. 26 and run approximately at right angles to one another in the implantation state of stent 1.

Figure 27:
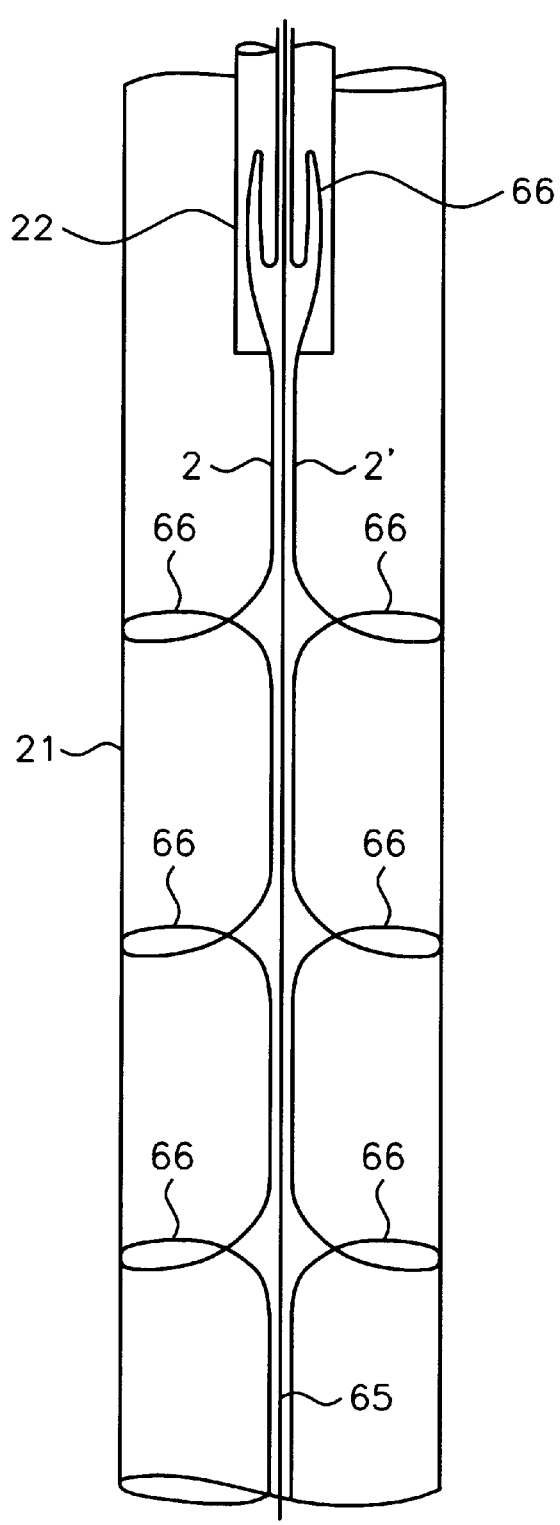
FIG. 27 shows a stent in another form of embodiment with spiral loops distanced from one another in the longitudinal direction of the stent.

FIG. 27 shows a stent 1 according to the invention in yet another form of embodiment, in which filaments 2, 2' are arranged parallel to one another over most of the longitudinal extent of stent 1, but are broadened into spiral loops 66, 66' opposed to one another at specific intervals. In the case of implantation of stent 1 by means of a catheter 22, spiral loops 66, 66' are bent and lie next to the parallel segments of filaments 2, 2'. Thus the axial distances between spiral loops 66, 66' on stent 1 are dimensioned such that axially adjacent spiral loops 66, 66' do not contact one another in the extended state of the stent, in order to keep the inner diameter of catheter 22, which is necessary for implantation, as small as possible. Like the stent shown in FIG. 25, the stent shown in FIG. 27 is also surrounded with a sheath 57, which preferably comprises a textile knit piece. As an alternative to the form of embodiment shown in FIG. 27, opposed spiral loops 66 may also be arranged on one side of the principal wire 65.

Figure 28:
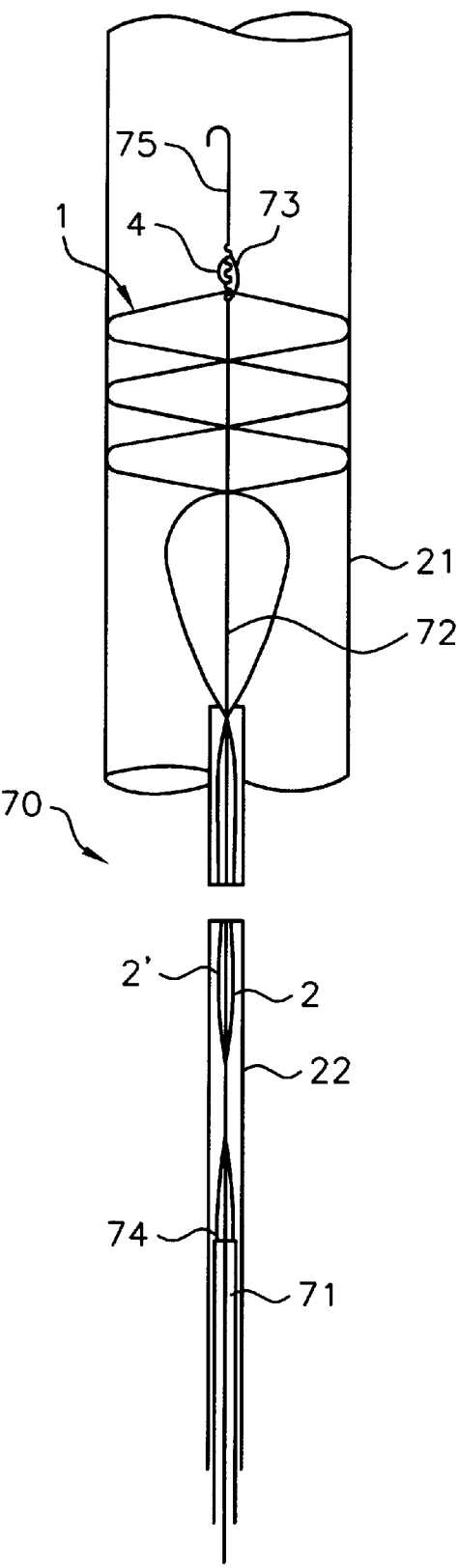
FIG. 28 shows a stent and a device for the implantation of a stent.

FIG. 28 finally shows an advantageous configuration of an implantation device 70. Stent 1 is thus introduced into body vessel 21 by means of a catheter 22 as a longitudinally extended double filament, and it assumes its predetermined double-spiral structure in the vessel. Two pushing devices 71, 72 are used, in order to bring stent 1 into its predetermined position. The outer pushing device 71 serves for the purpose of shifting stent filaments 2, 2' supported on its front end 74 through catheter 22 to a predetermined site in body vessel 21. A concentric lumen extends through outer pushing device 71, through which inner pushing device 72 is guided. Inner pushing device 72 is comprised of a thin, but rigid wire, which has a threaded segment 73 on its distal end and is joined by the latter with the distal end of stent 1. A flexible guide wire 75 is arranged at the distal end of threaded segment 73 of inner pushing device 72, and the tip of this wire 75 is bent in order to prevent lesions of the vessel when the inner pushing device is introduced into the vessel.

When stent 1 is introduced into vessel 21, first both pushing devices 71, 72 are advanced in the case of extended stent 1 in catheter 22. As soon as the first segment of stent 1 has assumed its predetermined double-spiral structure in the body vessel, the stent is held coaxially to the wall of vessel 21 by means of inner pushing device 72. A springing back or a springing forward of stent 1 in body vessel 21 is avoided thereby. Threaded segment 73 of inner pushing device 72 is joined rigidly, but detachably, with stent 1 on the end loop 4 joining the two filaments 2, 2' of stent 1 with one another. While catheter 22 is pulled back and simultaneously the stent is advanced by means of outer pushing device 71, the distal end of the stent is held by the inner pushing device 72. If stent 1 has been completely introduced into body vessel 21, inner pushing device 72 is detached from end loop 4 of stent 1. Of course, a thread on the stent tip could also be introduced in order to obtain a reliable attachment of inner pushing device 72 to stent 1. It is also conceivable that the outer pushing device 71 is joined at its front end 74 with stent 1 in a detachable manner, e.g., by means of a threaded screw connection. Such an embodiment makes it possible to again remove an implanted stent from a body vessel 21 after a certain implantation time. Instead of the coaxially arranged pushing devices 71, 72, another alternative form of embodiment of implantation device 70 provides these pushing devices next to each other in the catheter, whereby a first pushing device corresponding to inner pushing device 72 projects over the other by a predetermined length at its distal end.

Figure 29:
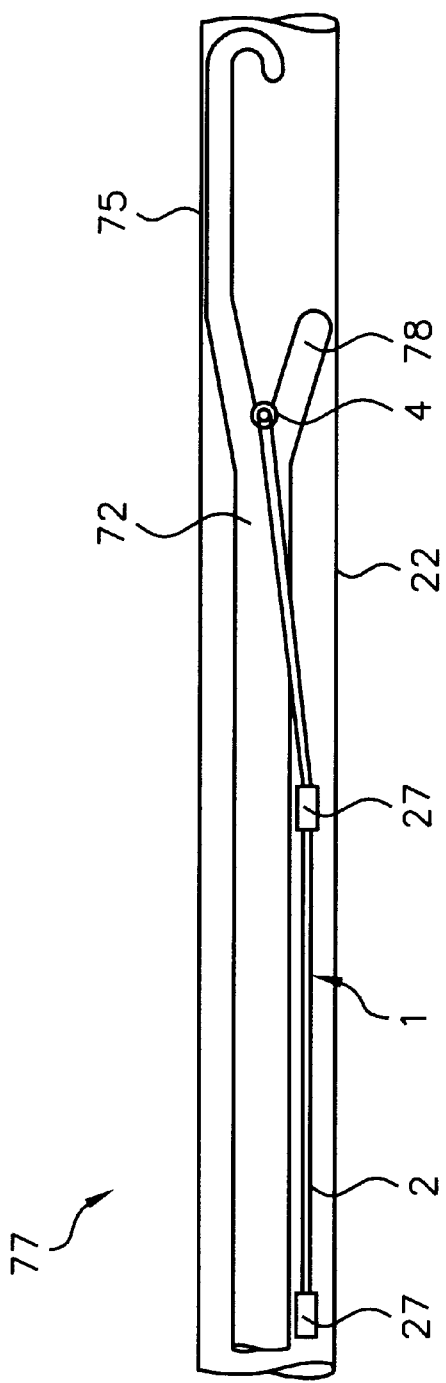
FIG. 29 shows a stent and an implantation device in another form of embodiment in a lateral view.

Implantation device 77 illustrated in FIG. 29 has a catheter 22 and a pushing device 72 that is taken up therein in an axially displaceable manner, which, like pushing device 72 of the implantation device from FIG. 28, is provided with a guide wire 75 bent at its distal end. At the front segment of pushing device 72 connecting to guide wire 75, a fork-shaped expansion 78 is arranged, which is provided with sleeves 27 for engaging the loops sealing filaments 2,2' of stent I to be implanted, at its distal end, or sleeves 27 joining filaments 2, 2' together.

Figure 30:
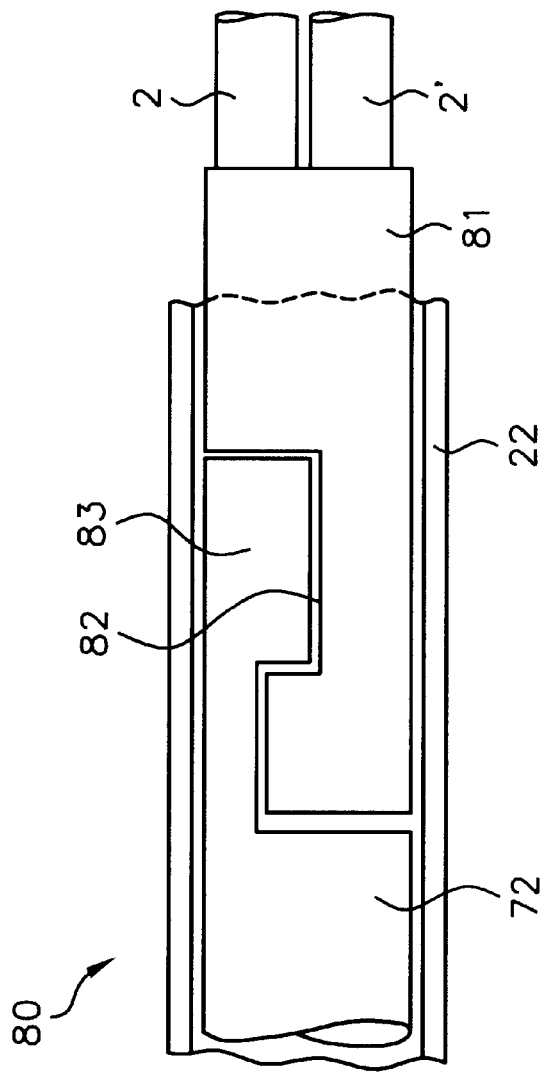
FIG. 30 shows a stent and an implantation device in yet another form of embodiment in the region of the proximal stent end during implantation.

After placement of catheter 22 in its correct position in body vessel 21—not shown in FIG. 29—stent 1 is advanced in the body vessel to loop 4 sealing filaments 2, 2' at the distal stent end, by means of pushing device 72. After the positionally correct placement of the distal end of the stent, pushing device 72 is guided back into catheter 22 to behind the next sleeve 27 joining filaments 2, 2'. As soon as pushing device 72 is again advanced, it engages the next sleeve 27 with its fork-shaped extension 78, with the consequence that the part of the stent found in the catheter at this sleeve 27 can be shifted out from catheter 22 by means of pushing device 72. A very reliable, positionally-correct placement of stent 1 in the body vessel is possible due to the successive activation of pushing device 72 at sleeves 27 joining filaments 2, 2' of stent 1. Whereas implantation device 77 shown in FIG. 29 operates on the distal end of the stent, a guiding of stent 1 at its proximal end is possible with implantation device 80 illustrated by excerpts in FIG. 30.

Implantation device 80 also has a catheter 22 and a pushing device 72 taken up in an axially movable manner therein. A hook element 83 is arranged at the distal end of the pushing device. Filaments 2, 2' of stent 1 to be implanted are simultaneously joined together at its proximal end by means of an end sleeve 81, which in turn is provided with a notch 82 running crosswise to the axial extent of the stent, which can be joined in lock-and-key manner with hook element 83 of pushing device 72.

During implantation, the distal end of the stent is pushed out from catheter 22 by means of pushing device 72.

Until stent 1 arrives at its final positionally-correct placement, its proximal end remains, however, in catheter 22 and is thus joined with pushing device 72 at its hook element 83 in an axially rigid manner. In this position, at any time, stent 1 can be completely pulled back into catheter 22.

Stent 1 is detached from pushing device 72 in a simple way by shifting the proximal end of stent 1 out from catheter 22 after stent 1 has been placed in its correct position in body vessel 21. Stent 1 and pushing device 72 are then moved freely opposite one another perpendicular to the axial extent of catheter 22 and end sleeve 81 can thus be detached from hook element 83.

Still another implantation device 85, which is provided for the exact placement of the distal stent end in a body vessel, is shown in FIGS. 31 and 32. The implantation device 85 is in turn provided with a catheter 22 and an axially displaceable pushing device 72 taken up therein. The pushing device has a forceps-shaped front segment 86, whose forceps elements 87, 87' engage the distal end of a stent I to be implanted, i.e., at a loop 4 sealing stent 1 on the distal side or at a sleeve 5, 27 joining the filaments 2, 2' of stent 1 at its distal end. In contrast to the implantation device 77 shown in FIG. 29, a forward and reverse motion of stent 1 is possible with the implantation device 85 shown in FIG. 31, by means of pushing device 72, whereby a possible erroneous positioning of the distal end of stent 1 in body vessel 21 can be corrected.

Stent 1 is successfully detached from pushing device 72 by first pulling catheter 22 back in body vessel 21 far enough so that at least one portion of the spiral loops of stent 1 develop into their predetermined implantation position, as this is illustrated in FIG. 32.

By repeated advance of catheter 22, the latter loads stent 1 in the axial direction with a force, shown by arrows in FIG. 32, which, facilitated by filaments 2, 2' at the distal end, leads to the circumstance that forceps elements 87, 87' are pressed apart and thus release loop 4.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A stent for treating pathological body vessels comprising at least two longitudinally extended filaments that can be delivered into a body vessel with an implantation device, the stent having a delivery state and an implanted state at the site of implantation such that at least two filaments form opposed spirals in the implanted state over at least a part of the longitudinal extent of the stent, each of the at least two filaments spiraling about the stent circumference in opposing directions, wherein at least one filament has an arc-shaped segment running along a periphery of the stent and wherein two filaments have an alternating structure in which at least one complete spiral loop follows at least one arc-shaped segment, and filaments are displaced such that a spiral loop of one filament crosses over an arc-shaped segment of a second filament.

2. The stent of claim 1, further characterized in that the filaments comprise of a material with a superelastic property or a thermo-memory property.

3. The stent of claim 1, further characterized in that the filaments of opposed spirals comprise a single filament wire, which has a bend at a joining site of the two spirals.

4. The stent of claim 1, further characterized in that the filaments of opposed spirals comprise a single piece.

5. The stent of claim 1, further characterized in that the filaments have the same direction of rotation over at least a part of the total length of stent.

6. The stent of claim 1, further characterized in that two filaments have arc-shaped segments opposed to one another at least over a part of the longitudinal extent of stent.

* * * * *